United States Patent [19]
Sclafani

[11] Patent Number: 5,890,899
[45] Date of Patent: Apr. 6, 1999

[54] DENTAL ISOLATOR

[75] Inventor: Adam Sclafani, North Canton, Ohio

[73] Assignee: Intellitech Corporation, New York, N.Y.

[21] Appl. No.: 883,820

[22] Filed: Jun. 27, 1997

[51] Int. Cl.⁶ .................................................. A61C 17/04
[52] U.S. Cl. ............................ 433/140; 433/93; 600/238
[58] Field of Search ............................ 433/93, 138, 139, 433/140; 600/237, 238, 239, 242

[56] References Cited

U.S. PATENT DOCUMENTS

| | | |
|---|---|---|
| 50,461 | 10/1865 | Dibble . |
| 63,709 | 4/1867 | Dibble . |
| 86,922 | 2/1869 | Hurd ........................................ 600/238 |
| 1,202,264 | 10/1916 | Brown . |
| 1,401,646 | 12/1921 | Rönn ......................................... 433/93 |
| 1,930,712 | 10/1933 | Girvin . |
| 2,102,263 | 12/1937 | Grunewald ................................ 433/94 |
| 2,103,115 | 12/1937 | Mizzy et al. ............................ 433/140 |
| 2,603,870 | 7/1952 | Nordin ..................................... 433/93 |
| 2,830,371 | 4/1958 | Dahl ........................................ 433/93 |
| 2,937,445 | 5/1960 | Erickson . |
| 3,148,449 | 9/1964 | Lanigan .................................... 433/93 |
| 3,396,468 | 8/1968 | Dayhoff . |
| 4,053,984 | 10/1977 | Moss ...................................... 433/140 |
| 4,215,984 | 8/1980 | Reichley .................................. 433/93 |
| 4,260,378 | 4/1981 | O'Neil ..................................... 433/93 |
| 4,544,357 | 10/1985 | Williams ................................ 433/136 |
| 4,802,851 | 2/1989 | Rhoades ................................... 433/93 |
| 4,975,057 | 12/1990 | Dyfvermark .............................. 433/93 |
| 4,992,046 | 2/1991 | Sharp ....................................... 433/93 |
| 5,199,872 | 4/1993 | Leal ....................................... 433/136 |
| 5,516,286 | 5/1996 | Kushner .................................... 433/93 |

FOREIGN PATENT DOCUMENTS

| | | | |
|---|---|---|---|
| 139610 | 11/1934 | Australia .............................. 600/237 |
| 650629 | 9/1937 | Germany .............................. 600/242 |

Primary Examiner—Ralph A. Lewis
Attorney, Agent, or Firm—Cohen, Pontani, Lieberman & Pavane

[57] ABSTRACT

The dental device includes a buccal member and a lingual member disposable on one side of a patient's mouth for isolating the buccal and lingual sides of the patient's mandibular teeth, respectively. The buccal member is generally curved to follow an outer contour of the patient's mandibular arch for deflecting the patient's cheek from the buccal side of the mandibular teeth. The lingual member is configured to corral a side of the patient's tongue and has a neck portion in a region where the lingual member attaches to the buccal member, the neck portion being configured to rest on the patient's mandibular teeth. The distal ends of the buccal and lingual members are spaced apart to permit independent movement therebetween. In one embodiment, the device includes a prop stem releasably attachable to the patient's maxillary teeth for propping open the patient's mouth. The embodiment is constructed such that the buccal member depends angularly from a bottom section of the prop stem and the lingual member extends from the bottom section of the prop stem and away from the buccal member. In another embodiment, the device may include, instead of the prop stem, an elongated chin bar for releasable attachment with the patient's lower jaw. According to this embodiment, the chin bar extends downwardly from the buccal and lingual members and has a bottom section configured to corral the patient's chin.

13 Claims, 11 Drawing Sheets

DENTAL ISOLATOR

BACKGROUND OF THE INVENTION

1. Field of the Invention

The present invention relates to dental appliances and, more particularly, to a dental device positionable in a patient's mouth for isolating a portion thereof.

2. Description of the Prior Art

A dentist encounters many problems when performing dental services on a patient. One problem is that the patient must, of course, maintain his mouth open to permit access for the duration of the procedure. Another problem is that the patient's cheek and tongue may obstruct the treatment area. Still another problem is that the patient's mouth produces fluids which may obscure the treatment area and/or interfere with proper bonding of dental substances such as, for example, amalgam. Pieces of tooth and/or amalgam freed by drilling also must be dealt with during the course of treatment.

To maintain the subject tooth dry and isolated, the dentist typically places a cotton roll adjacent the tooth and positions a plastic suction tube in the patient's mouth, most often by hanging it over the lower lip. The suction tube inlet is typically positioned near the patient's tongue so that fluids and/or solids disposed thereabout can be evacuated. To further maintain the mouth clean and dry, a dental assistant may insert another suction tube into the mouth to aspirate fluids from areas unaffected by the first-mentioned suction tube.

Another device for isolating a tooth is the rubber dam. The rubber dam is a flexible piece of material having at least one hole defined therein such that it may be placed down over the tooth and into surface contact with the gums so that the tooth protruding through the hole is isolated from adjacent tissue.

For maintaining the patient's mouth in the open position a dentist may employ a bite block or expansion forceps.

OBJECTS AND SUMMARY OF THE INVENTION

An object of the present invention is to provide a low-cost dental device, releasably securable to a patient's mouth, for isolating a portion of the patient's mouth.

Another object of the invention is to provide a low-cost integral dental device having buccal and lingual members with spaced-apart distal ends for effective isolation of the patient's mandibular arch.

Still another object of the invention is to provide a dental device having a prop stem releasably securable to the patient's maxillary arch to maintain a patient's mouth open.

Yet another object of the invention is to provide a dental device having a chin bar for releasably securing the device to a patient's lower jaw.

Still yet another object of the invention is to provide a dental device formed of a pliable material so that it can conform to the specific contour and size of a patient's mouth.

In accordance with an embodiment of this invention, the dental device includes a prop stem, an upper maxillary support, a buccal member and a lingual member. The upper maxillary support is secured to a top section of the prop stem and is configured to support a maxillary arch of the patient's mouth. The buccal member depends angularly from a bottom section of the prop stem and is generally curved so as to follow an outer contour of the mandibular arch of the patient's mouth. The lingual member extends from the bottom section of the prop stem and away from the buccal member and is configured to corral a side of the patient's tongue. The lingual member has a neck portion at a region where the lingual member connects with the prop stem, the neck portion being shaped to rest on the mandibular arch of the patient's mouth. A distal end of the buccal member is spaced apart from a distal end of the lingual member such that the distal ends of the buccal and lingual members are disposable on opposite sides of the patient's mandibular arch.

According to a feature of the embodiment, the distal end of at least one of the buccal member and the lingual member has a projecting portion shaped for releasable attachment with a device for aspirating fluids from the patient's mouth. The dental device further includes an aspirating device disposed adjacent at least one of the buccal member and the lingual member, the aspirating device including a releasable attaching means for releasably attaching the aspirating device to the projecting portion. The aspirating device may include a suction tube having a side wall defining a conduit therethrough and a plurality of apertures in the side wall in communication with the conduit. The releasable attaching means may include a ring connected to a distal end of the suction tube, the ring having an opening sized for receiving the projecting portion.

According to another feature of the embodiment, the dental device further includes a movable adjusting means for securing the upper maxillary support to the top section of the prop stem for movement relative thereto for adjusting an axial distance between the upper maxillary support and the top section. The movable adjusting means may include a threaded stud extending from one of the top section of the prop stem and the upper maxillary support and a mating internally threaded sleeve extending from the other of the top section and the upper maxillary support such that the prop stem and the upper maxillary support are in threaded engagement, whereby relative rotation of the upper maxillary support and the prop stem adjusts the axial distance therebetween. Alternatively, the movable adjusting means may include a threaded stud extending from the top section of the prop stem and a mating internally threaded sleeve extending from the upper maxillary support such that the prop stem and the upper maxillary support are in threaded engagement, and further including a means for rotatively coupling the upper maxillary support to the threaded sleeve, whereby relative rotation of the threaded sleeve and the threaded stud adjusts the axial distance between the upper maxillary support and the prop stem without relative rotation therebetween.

According to still another feature of the embodiment, the upper maxillary support comprises a U-shaped member for supporting the patient's maxillary arch and the dental device further comprises a resilient layer disposed on an outer surface of the buccal member and/or the lingual member. In addition, the buccal member and/or the lingual member may include a pliable material for selectively configuring the buccal member and/or the lingual member to conform to the patient's mouth.

According to an aspect of the embodiment, the prop stem may include a first sidewall defining a first conduit therethrough and a first aperture in the first sidewall in communication with the first conduit, and wherein the buccal member comprises a second sidewall defining a second conduit therethrough and a second aperture in the second sidewall in communication with the second conduit, the first and second conduits being in fluid communication such that fluids may be channeled through a fluid circuit comprising the first and second conduits and the first and second apertures.

According to another aspect of the embodiment, the prop stem comprises a first sidewall defining a first conduit therethrough and a first aperture in the first sidewall in communication with the first conduit, and wherein the lingual member includes a second sidewall defining a second conduit therethrough and a second aperture in the second sidewall in communication with the second conduit, the first and second conduits being in fluid communication such that fluids may be channeled through a fluid circuit comprising the first and second conduits and the first and second apertures.

According to still another aspect of the embodiment, the lingual member comprises a third sidewall defining a third conduit therethrough and a third aperture in the third sidewall in communication with the third conduit, the first conduit being in fluid communication with the third conduit such that fluids may be channeled through another fluid circuit comprising the first and third conduits and the first and third apertures.

In accordance with another embodiment of this invention, the dental device includes a buccal member, a lingual member, and an elongated chin bar. The buccal member is generally curved to follow an outer contour of a mandibular arch of the patient's mouth. The lingual member is shaped to corral a side of the patient's tongue and is connected with and extends angularly from the buccal member. The lingual member includes a neck portion in a region where the lingual member is connected with the buccal member, the neck portion being configured to rest on the patient's mandibular arch. The elongated chin bar extends downwardly from the lingual and buccal members and has a bottom section configured to corral the patient's chin.

According to a feature of this embodiment, the chin bar, the buccal member and/or the lingual member comprises a pliable material for selectively configuring the chin bar, the buccal member and/or the lingual member to the patient's mouth. The dental device further includes a resilient layer disposed on an outer surface of the chin bar, the buccal member, and/or the lingual member.

According to another feature of this embodiment, each of the buccal member and the lingual member has a distal end, the distal end of the buccal member and/or the lingual member has a projecting portion shaped for releasable attachment with a device for aspirating fluids from the patient's mouth. The aspirating device is disposed adjacent the buccal member and/or the lingual member and includes a releasable attaching means for releasably attaching the aspirating device to the projecting portion.

According to still another aspect of this embodiment, the aspirating device includes a suction tube defining a conduit therethrough and a plurality of apertures in the side wall in communication with the conduit. The releasable attaching means includes a ring connected to a distal end of the suction tube, the ring having an opening sized for receiving the projecting portion.

According to an aspect of the present invention, the chin bar comprises a first sidewall defining a first conduit therethrough and a first aperture in the first sidewall in communication with the first conduit, and wherein the buccal member comprises a second sidewall defining a second conduit therethrough and a second aperture in the second sidewall in communication with the second conduit, the first and second conduits being in fluid communication such that fluids may be channeled through a fluid circuit comprising the first and second conduits and the first and second apertures.

According to another aspect of this embodiment, the chin bar comprises a first sidewall defining a first conduit therethrough and a first aperture in the first sidewall in communication with the first conduit, and wherein the lingual member comprises a second sidewall defining a second conduit therethrough and a second aperture in the sidewall in communication with the second conduit, the first and second conduits being in fluid communication such that fluids may be channeled through a fluid circuit comprising the first and second conduits and the first and second apertures.

According to still another aspect of this embodiment, the lingual member includes a third sidewall defining a third conduit therethrough and a third aperture in the third sidewall in communication with the third conduit, the first conduit being in fluid communication with the third conduit such that fluids may be channeled through another fluid circuit comprising the first and third conduits and the first and third apertures.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and, as such, are merely conceptual in disclosing the presently preferred embodiments of the invention.

BRIEF DESCRIPTION OF THE DRAWINGS

In the drawings, wherein like reference characters denote similar elements throughout the several views.

DETAILED DESCRIPTION OF THE PRESENTLY PREFERRED EMBODIMENTS

Figure 1:
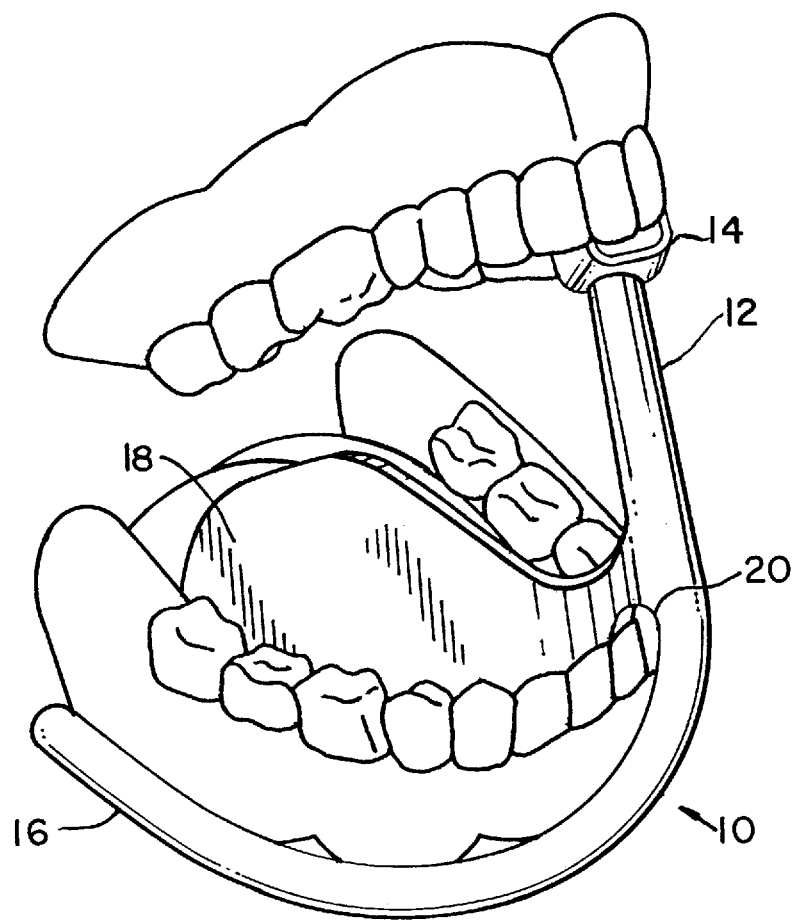
FIG. 1 is a perspective view of an embodiment of a dental device constructed in accordance with the present invention.
Figure 3:
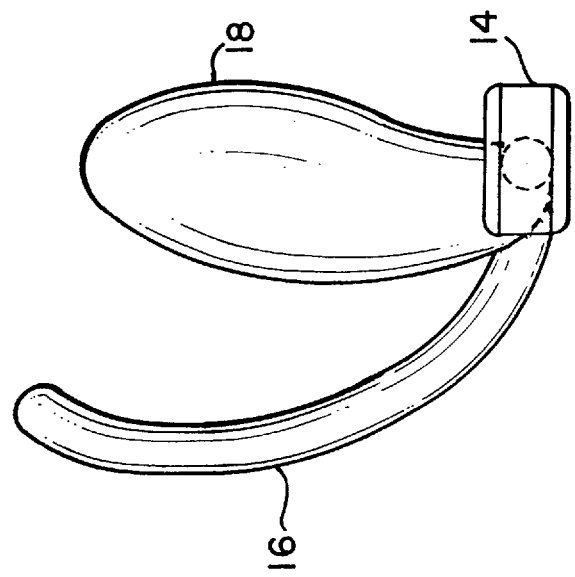
FIG. 3 is a top view of the embodiment of FIG. 1.
Figure 2:
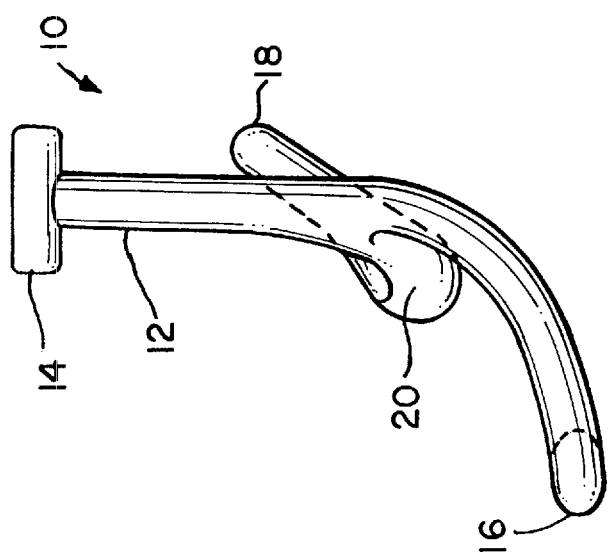
FIG. 2 is a front view of the embodiment of FIG. 1.

Referring now to the drawings, FIG. 1 depicts a right-sided version of an embodiment of the dental device 10 of the present invention disposed in the right side of a patient's mouth for isolating the right side of the patient's mandibular arch. Although only the right-sided version of a dental device in accordance with the present invention is discussed in detail herein, it will be appreciated that a left-sided version of the dental device 10 may also be provided. As shown in FIGS. 1–3, the dental device 10 includes a prop stem 12 for propping a patient's mouth open, an upper maxillary support 14 secured to a top section of prop stem 12 and configured to releasably support the maxillary arch of the patient, a buccal member 16 depending angularly from a bottom section of prop stem 12 for displacing the patient's cheek from the right side of the mandibular arch of the patient, and a lingual member 18 extending from a bottom section of the prop stem 12 and away from the buccal member 16 for deflecting the patient's tongue laterally from the patient's mandibular arch. The buccal and lingual members 16, 18 are spaced apart such that they are disposable on opposite sides of the patient's mandibular arch.

Prop stem 12 is dimensioned to span the opening of the patient's mouth such that adequate working space is provided for the dentist. Prop stem 12 has the requisite rigidity to resist bending, breaking or fracturing by typical clamping forces exerted by a patient's jaws.

Projecting from the top of the prop stem 12 is an upper maxillary support 14 for releasably securing the device 10 to the maxillary arch of the patient's mouth. The upper maxillary support 14 is preferably a generally U-shaped member so that at least a portion of the maxillary teeth may be partially confined therein for removably securing the top end of prop stem 12 to the patient's maxillary arch.

Figure 4:
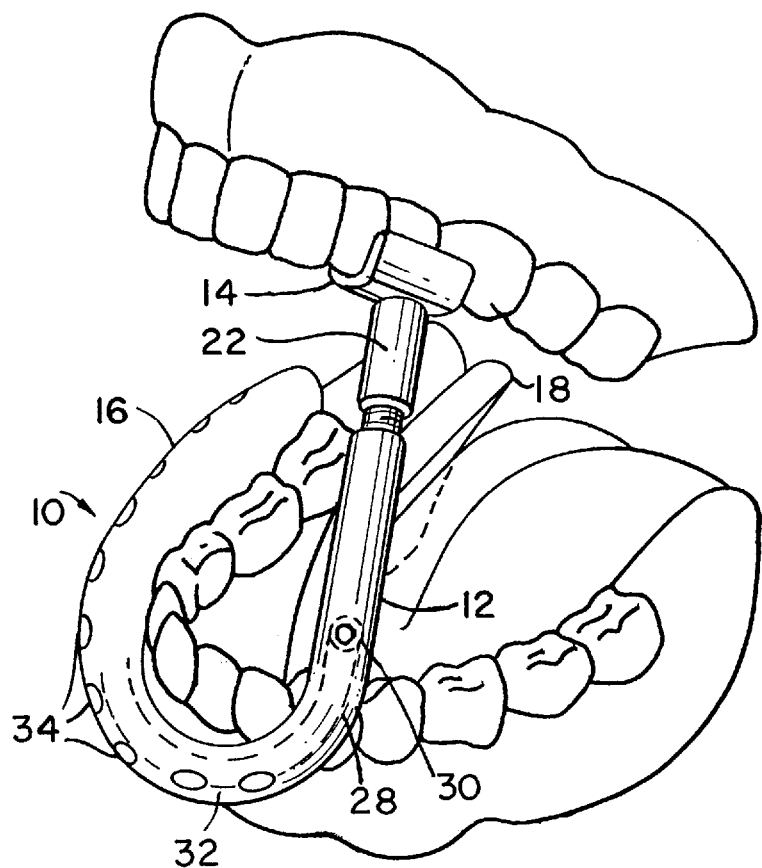
FIG. 4 is a perspective view of the embodiment of FIG. 1 and showing a fluid circuit and an adjustable stem.
Figure 5:
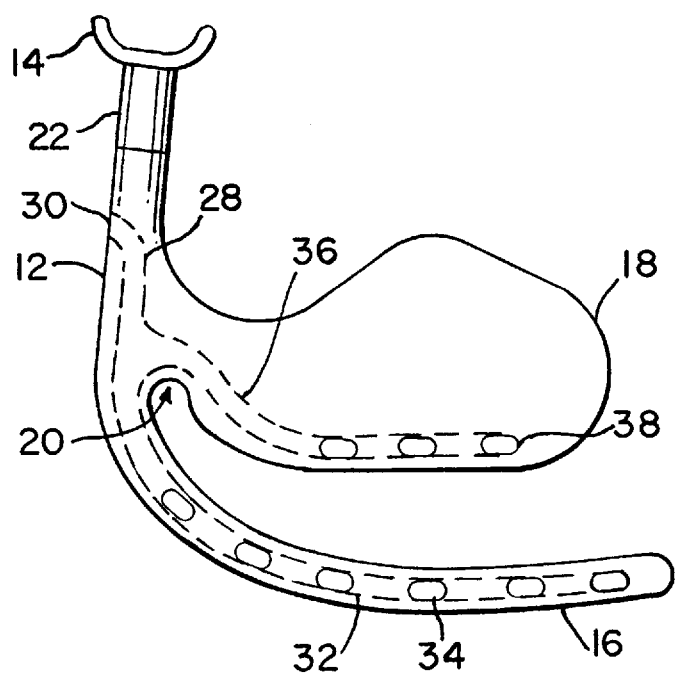
FIG. 5 is a left side view of the embodiment of FIG. 4.

FIGS. 4 and 5 illustrate a feature of the dental device 10 comprising a mechanism for selectively varying the length of the stem 12. The adjustment mechanism may include complementary threaded portions projecting from confronting surfaces of the upper maxillary support 14 and the prop stem 12 such that relative rotation of support 14 and prop stem 12 adjusts the axial distance therebetween. For example, the prop stem 12 may include a threaded stud 21 extending from the top thereof and an internally threaded sleeve 22 depending from the bottom of the maxillary support 14. Thus, by rotating, for example, sleeve 22 in one direction or the other, support 14 is moved axially upward or downward, thereby adjusting the axial distance between support 14 and prop stem 12.

Figure 6:
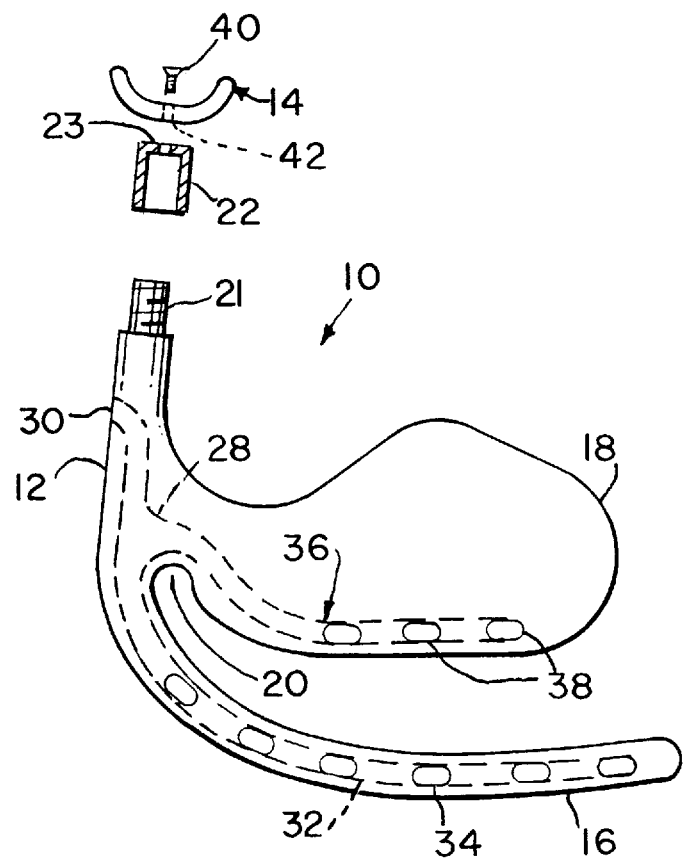
FIG. 6 is a left side view of the embodiment of FIG. 1 and showing a rotative coupling for the adjustable stem.

FIG. 6 illustrates an alternative adjustment mechanism, wherein upper maxillary support 14 and sleeve 22 are rotatively coupled to each other so that rotation of sleeve 22 does not rotate upper support 14, thereby accommodating adjustment of the length of prop stem 12 in situ. As illustrated, the stem of a screw 40 or the like extends through an opening 42 in the upper support 14 for unimpeded rotation therein, the stem being received in a blind threaded hole 23 in the top wall of sleeve 22. Thus, the rotative coupling facilitates relative rotation of the threaded sleeve 22 and the threaded stud 21 to adjust the axial distance between the upper maxillary support 14 and the prop stem 12 without relative rotation therebetween.

Referring again to FIGS. 1–3, the buccal member 16 is preferably curved and dimensioned to follow generally an outer contour of a mandibular arch of the patient. The buccal member 16 serves to isolate the buccal side of the mandibular arch and may be flat or cylindrically shaped. To ensure adequate isolation of the buccal side of the teeth, the cross-sectional diameter of the buccal member 16 may also be dimensioned so as to deflect the patient's cheek a desired distance away from the mandibular arch. The buccal member 16 is preferably made pliable by, for example, including a yieldable or deformable body along the length of the buccal member 16 so that the buccal member 16 may be bent or shaped to deflect the cheek of the patient from the buccal side of the teeth. It is contemplated that the yieldable body may be in the form of a properly sized wire embedded in the buccal member 16 or attached thereto.

The lingual member 18 may be generally curved and plate-like in shape and configured to corral a side of the patient's tongue. The lingual member 18 serves to isolate the lingual side of the teeth by deflecting laterally the tongue a distance from the mandibular arch. The lingual member 18 advantageously accomplishes this function without depressing the tongue or the floor of the mouth, which action could cause the patient to gag. Similar to the buccal member 16, the lingual member 18 may also be made pliable by, for example, attaching a yieldable or deformable body to the lingual member 18 or embedding the body therein.

As shown in FIGS. 4–6, dental device 10 may further include a fluid circuit comprising a plurality of apertures and conduits defined in prop stem 12, buccal member 16 and/or lingual member 18 for aspirating fluids from the patient's mouth. For example, prop stem 12 has a side wall defining a first conduit 28 and a first aperture (e.g. outlet opening) 30 in the sidewall in fluid communication with the first conduit 28. First aperture 30 may be threaded or otherwise configured for attachment with a vacuum tube (not shown) for drawing fluids from the fluid circuit. The buccal member 16 has a side wall defining a second conduit 32 therethrough and a plurality of second apertures (e.g. inlet openings) 34 in the side wall in communication with the second conduit 32. The lingual member 18 has a side wall defining a third conduit 36 therethrough and a plurality of third apertures (e.g. inlet openings) 38 in the side wall in communication with the third conduit 36. The first, second and third conduits 28, 32, 36 are in fluid communication for channeling the patient's fluids through a fluid circuit including the first, second and third conduits 28, 32, 36 and the first, second and third apertures 30, 34, 38.

Figure 7:
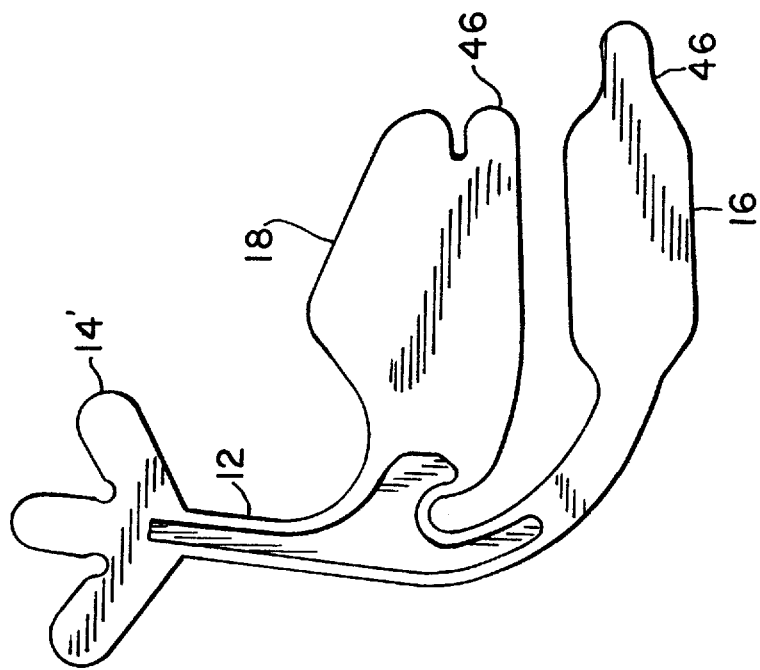
FIG. 7 is a plan view of a stamped pattern of the embodiment of FIG. 1.
Figure 7A:
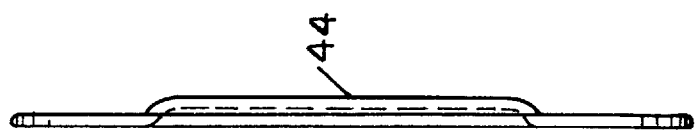
FIG. 7A is a side view of the stamped pattern of FIG. 7.

It is contemplated that the dental device 10 may be formed as a unitary structure by way of injection molding or the like. Such a construction lowers production costs and moreover, permits easy sterilization or disinfection for reuse since such a construction would have minimal or no crevices in which microbes can hide and breed. To accommodate different oral cavities of patients, various sizes of dental device 10 can, of course, be manufactured. As shown in FIGS. 7 and 7A, device 10 may also be produced by a machining operation known as "stamping" wherein a predetermined pattern or shape is stamped or cut from a sheet of metal such as, for example, aluminum. Upper support 14' in this embodiment may be shaped as a tripod-like structure. To increase bending rigidity of stem 12 and/or neck portion 20, the cross-sectional dimension thereof may be increased by, for example, forming an outwardly-pushed section or embossment 44. The stamped part is subsequently configured into its functional form as depicted in FIG. 8.

Figure 8:
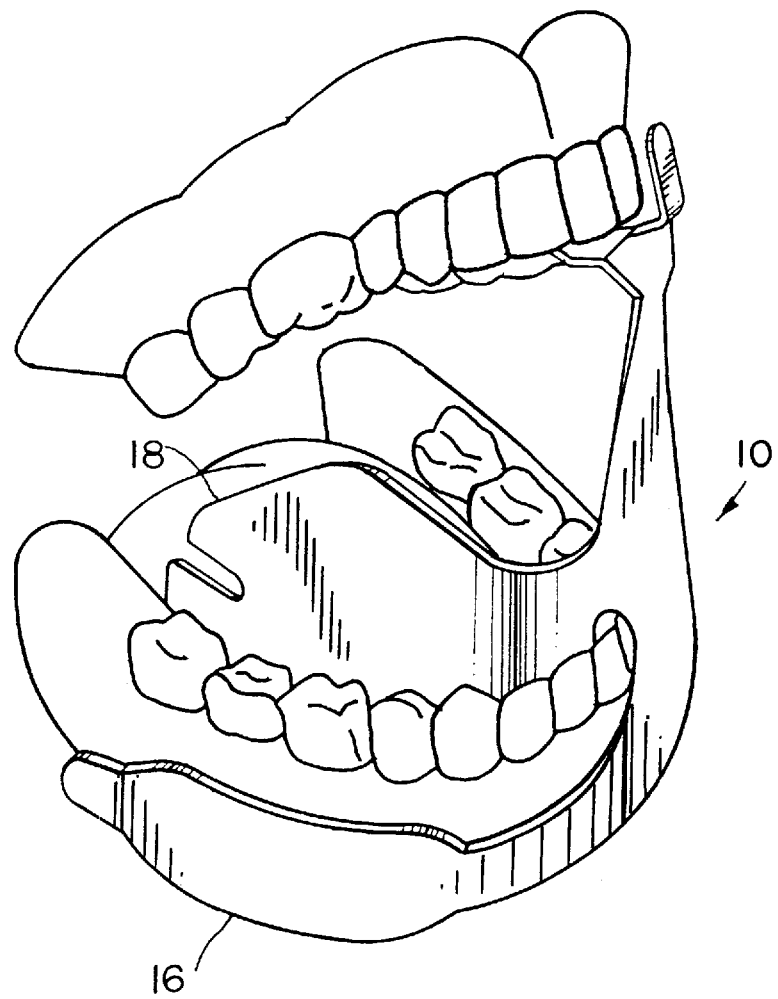
FIG. 8 is a perspective view of the embodiment configured from the stamped pattern of FIG. 7.
Figure 9:
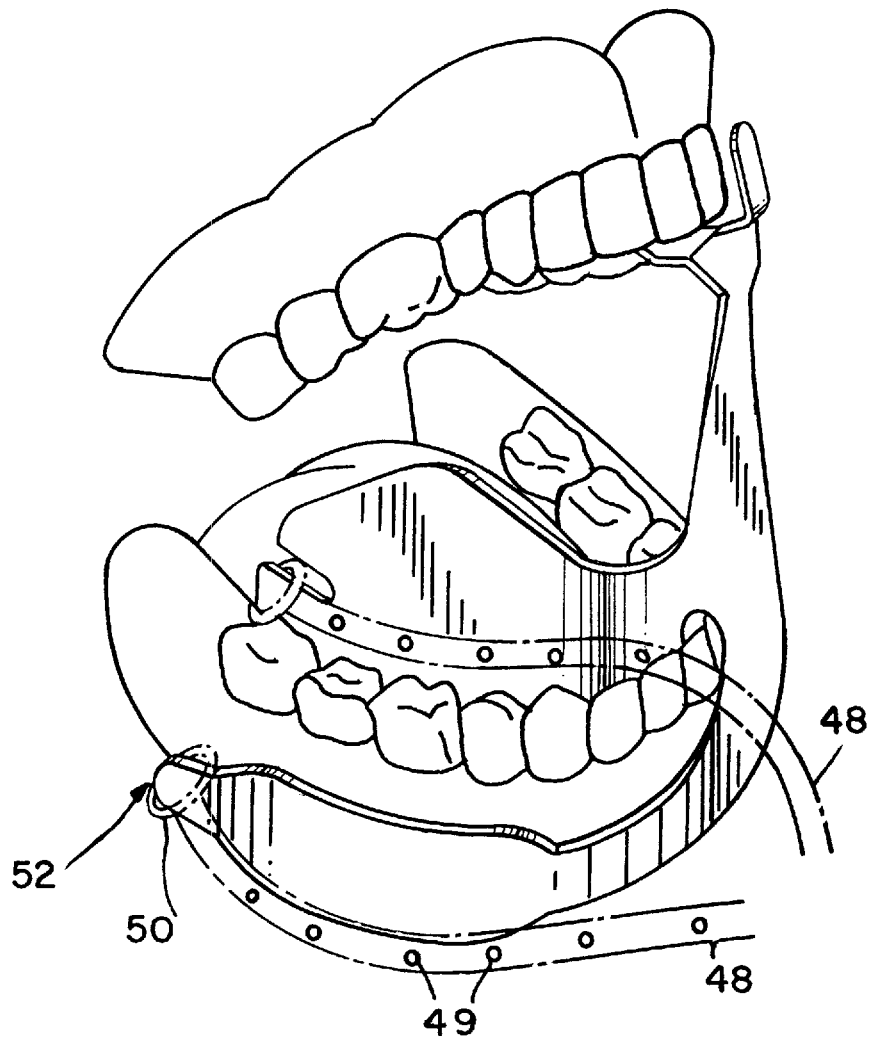
FIG. 9 is a perspective view of the embodiment of FIG. 8, showing suction tubes releasably attached to the device.

As seen in FIGS. 7–9, the buccal and lingual members 16, 18 may include a projecting portion 46 at each of their distal ends shaped for releasable attachment with a device such as, for example, a suction tube 48 having a plurality of apertures 49 along its longitudinal axis for aspirating fluids from the patient's mouth. The suction tube 48 may include a ring-like structure 50 having an annular opening 52 that is sized for frictional receipt of the projecting portion 46 for releasably attaching the suction tube 48 to the buccal and/or lingual members 16, 18.

In use, a dentist may removably secure, for example, a left-sided version of the dental device 10 in a patient's mouth by positioning the buccal and lingual members 16, 18 along the buccal and lingual sides of the patient's mandibular arch, resting the neck portion 20 of the lingual member 18 on the patient's mandibular teeth and manipulating the upper support 14 to receive the patient's upper maxillary teeth as the patient closes his mouth. The device 10 is thereby releasably secured to the patient's mouth. If the dental device has pliable buccal and lingual members 16, 18, the dentist may precisely shape, orient or conform these members to fit the particular contours of the patient. If the embodiment of dental device 10 provides conduits 28, 32, 36 therewithin, the user may attach a vacuum tube to the outlet opening 30 in the prop stem 12 for aspirating fluids from the patient's mouth.

Figure 10:
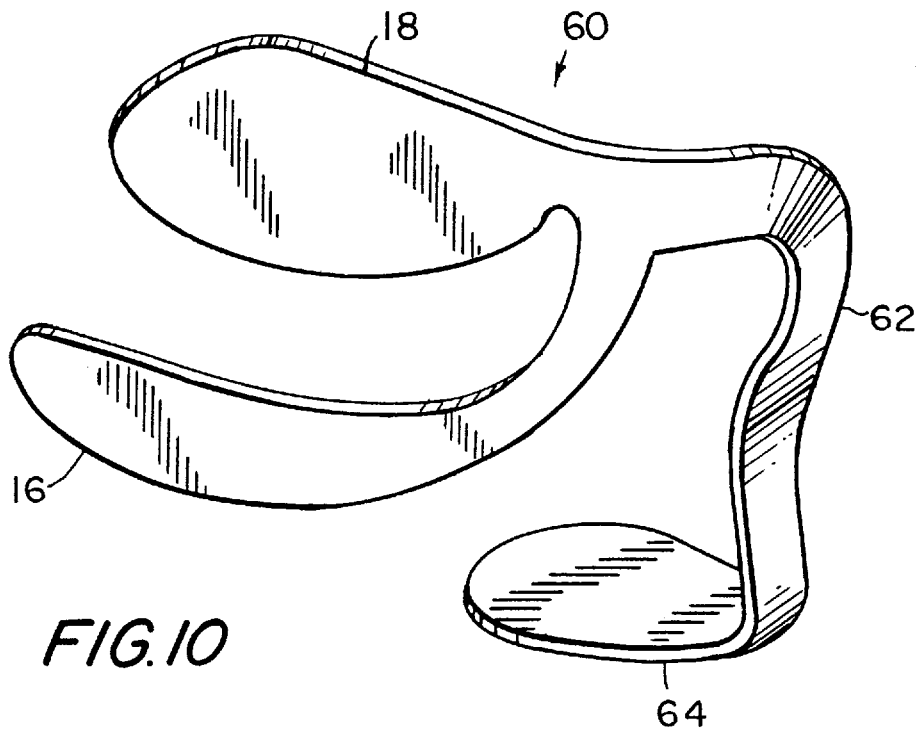
FIG. 10 is a perspective view of another embodiment of a dental device, constructed in accordance with the present invention.

In accordance with another embodiment of the present invention and as shown in FIG. 10, the dental device 60 also includes buccal and lingual members 16, 18, but instead of or in addition to prop stem 12, device 60 has an elongated chin bar 62 extending downwardly from the lingual and buccal members 16, 18 for releasably securing device 60 to the patient's lower jaw. The chin bar 62 has a bottom section 64 configured to corral or grip the patient's chin. The chin bar 62 is preferably made pliable as was described above so that it can be selectively shaped to a patient's lower jaw.

Figure 13:
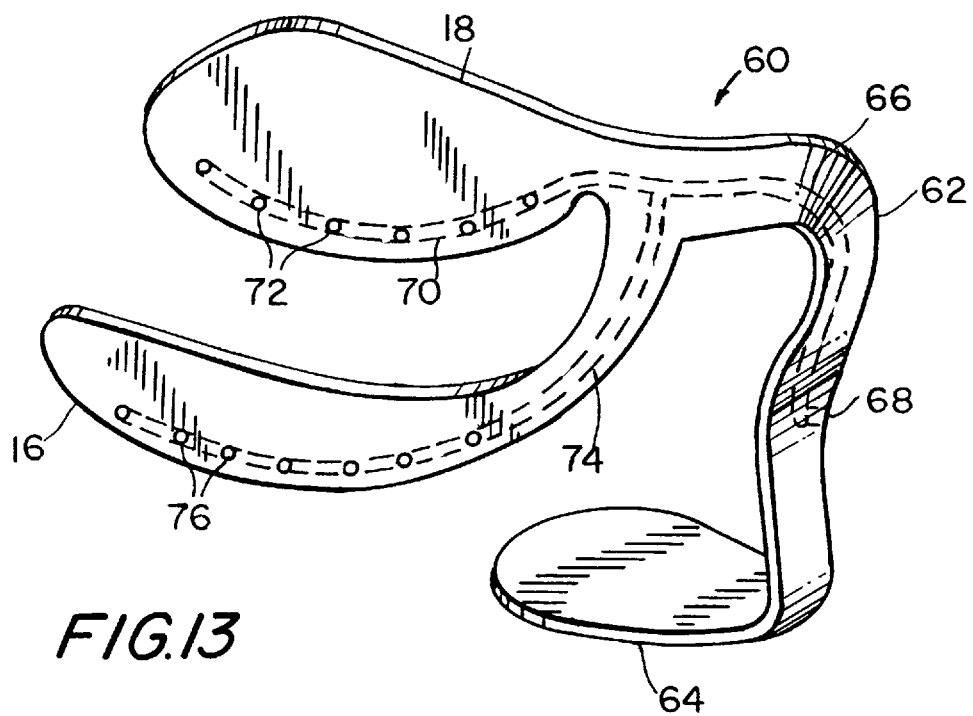
FIG. 13 is a perspective view of the embodiment of FIG. 10 and showing a fluid circuit.

Again, as in the embodiments of FIGS. 4–6, the dental device 60 depicted in FIG. 13 may further include a fluid circuit comprising a plurality of apertures and conduits defined in the chin bar 62, the buccal member 16 and/or the lingual member 18 for aspirating fluids from the patient's mouth. In this embodiment, the chin bar 62 has a side wall defining a first conduit 66 and a first aperture (e.g. outlet opening) 68 in the sidewall in fluid communication with the first conduit 66. First aperture 68 may be threaded for attachment with a vacuum tube (not shown). The lingual member 18 has a side wall defining a second conduit 70 therethrough and a plurality of second apertures (e.g. inlet openings) 72 in the side wall in communication with second conduit 70. The buccal member 16 has a side wall defining a third conduit 74 therethrough and a plurality of third apertures (e.g. inlet openings) 76 in the side wall in communication with the third conduit 74. The first, second and third conduits 66, 70, 74 are in fluid communication for channeling the patient's fluids through the fluid circuit comprising the first, second and third conduits 66, 70, 74 and the first, second and third apertures 68, 72, 76.

Figure 11:
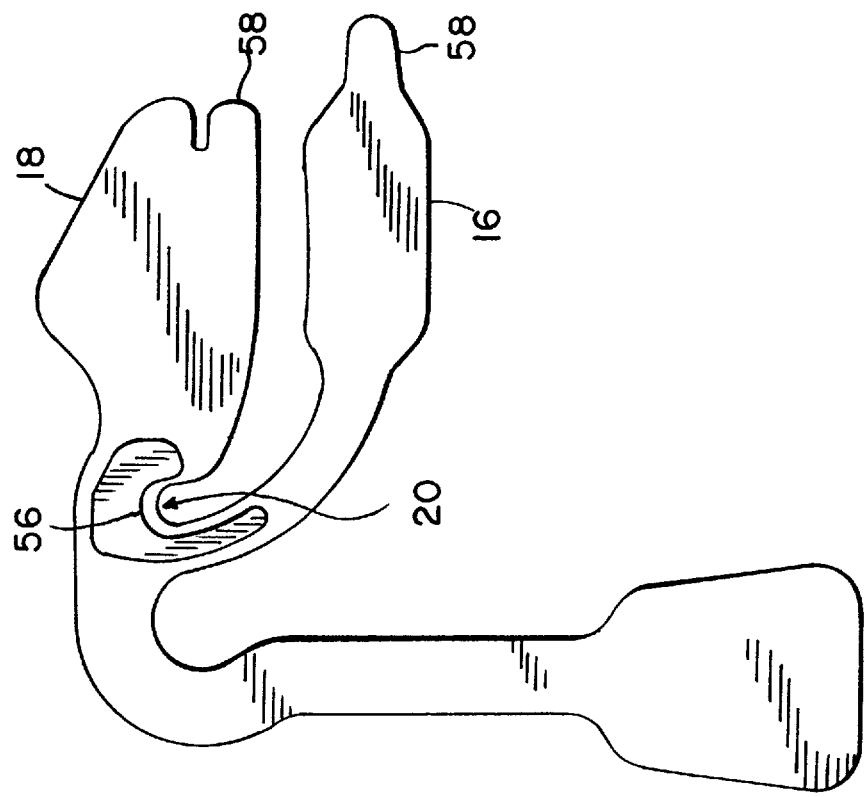
FIG. 11 is a plan view of a stamped pattern of the embodiment of FIG. 10.
Figure 11A:
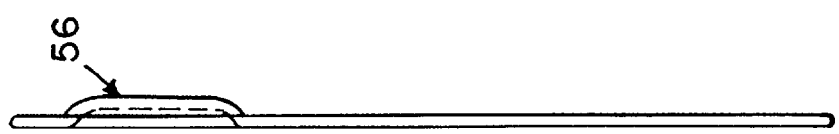
FIG. 11A is a side view of the stamped pattern of FIG. 11.

Dental device 60 may also be formed as a unitary structure by way of injection molding or the like. To accommodate individual patients, various sizes of device 60 can also be produced. As shown in FIGS. 11 and 11A, device 10 may be produced by stamping wherein a predetermined shape is cut from a sheet of metal such as, for example, aluminum. To increase bending rigidity of the neck portion 20, the cross-sectional size of the chin bar 62 may be increased by, for example, forming an outwardly-deformed section or embossment 56 therein. The stamped part may be shaped into its functional form as depicted in FIG. 12.

Figure 12:
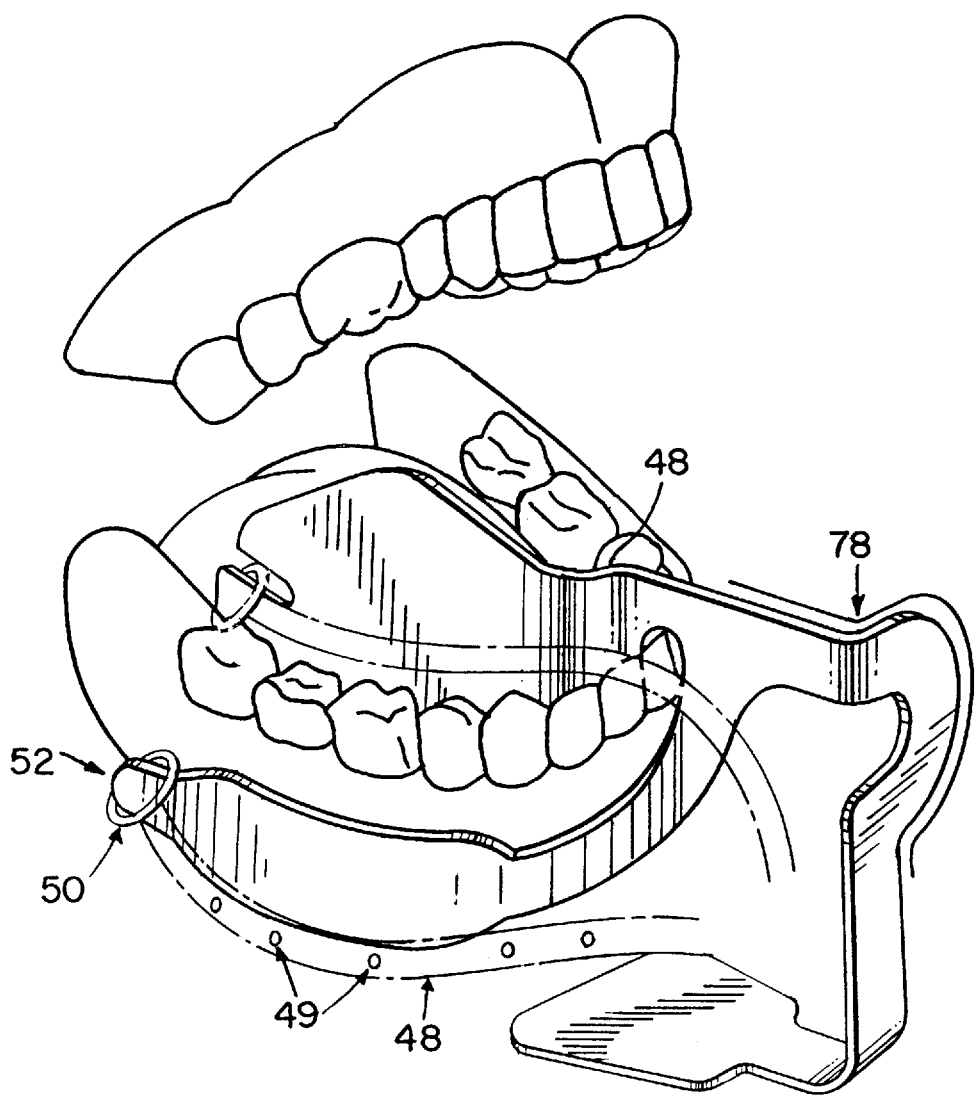
FIG. 12 is a perspective view of the embodiment configured from the stamped pattern of FIG. 11.

Similar to the embodiment shown in FIG. 9, the buccal and lingual members 16, 18 of device 60 may also include a projecting portion 58 at each of their distal ends (as illustrated in FIG. 12). The projecting portion 58 is shaped for releasable attachment with a device such as, for example, suction tube 48 for aspirating fluids from the patient's mouth. The suction tube 48 may include a ring-like structure 50 connected to an end of the tube. The ring-like structure 50 has an annular opening 52 that is sized for frictional engagement of the projecting portion 58 for releasably attaching the suction tube 48 to the buccal and/or lingual members 16, 18.

As shown in FIG. 12, the device 10 and/or ring-like structure 50 may further include a resilient layer 78 such as, for example, silicone or the like disposed or otherwise attached to an outer surface of device 10 or ring-like structure 50 for increasing the level of comfort to the patient as well as for protecting oral tissues from injury.

In use, the buccal and lingual members 16, 18 of device 60 may be placed in the patient's mouth as was described for device 10. But instead of relying on a prop stem and a maxillary support for releasable attachment with the patient's mouth, device 60 utilizes the chin bar 62 to anchor the device to the patient's lower jaw by conforming or gripping bottom section 64 to the underside of the patient's chin. Thus disposed, bottom section 64 of chin bar 62 imparts a slight clamping force to the patient's chin while neck portion 20 of chin bar 62 imparts an opposing clamping force onto the patient's mandibular teeth. If the particular embodiment provides for a pliable chin bar, the dentist may precisely conform the chin bar 62 to the specific contour of the patient's chin for improved anchoring.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A dental device for isolating a portion of a patient's mandibular arch, comprising:

a prop stem having an elongated body with a top section at one end and a bottom section at another end, said prop stem being dimensioned to span the opening of the patient's mouth;

an upper maxillary support having a generally U-shaped body secured to the top section of said prop stem, the generally U-shaped body being releasably securable to the maxillary arch of the patient's mouth;

a buccal member having a pliable elongated body depending angularly downwardly from the bottom section of said prop stem and generally curved so as to follow an outer contour of said portion of the mandibular arch of the patient's mouth, said buccal member being adapted to displace the patient's cheek a distance from the mandibular arch of the patient; and a lingual member having a pliable plate-like body extending angularly downwardly from the bottom section of said prop stem and generally curved to follow along an inner contour of said portion of the mandibular arch of the patient away from said buccal member, said lingual member being configured to corral a side of the patient's tongue and to deflect laterally said side of the patient's tongue a distance from an adjacent surface of the mandibular arch, said lingual member having a neck portion at a region where said lingual member extends from the bottom section of said prop stem, said neck portion being shaped to rest on the mandibular arch of the patient's mouth.

2. The dental device of claim 1, wherein said distal end of at least one of said buccal member and said lingual member has a projecting portion shaped for releasable attachment with a device for aspirating fluids from the patient's mouth.

3. The dental device of claim 2, further comprising an aspirating device disposed adjacent at least one of said buccal member and said lingual member, said aspirating device including releasable attaching means for releasably attaching said aspirating device to said projecting portion.

4. The dental device of claim 3, wherein said aspirating device includes a suction tube having a side wall defining a conduit therethrough and a plurality of apertures in said side wall in communication with said conduit.

5. The dental device of claim 4, wherein said releasable attaching means includes a ring connected to a distal end of said suction tube, said ring having an opening sized for receiving said projecting portion.

6. The dental device of claim 1, further comprising a resilient layer disposed on an outer surface of at least one of said buccal member and said lingual member.

7. The dental device of claim 1, further comprising movable adjusting means for securing said upper maxillary support to the top section of said prop stem for movement relative thereto for adjusting an axial distance between said upper maxillary support and said top section.

8. The dental device of claim 7, wherein said movable adjusting means includes a threaded stud extending from one of said top section of said prop stem and said upper maxillary support and a mating internally threaded sleeve extending from the other of said top section and said upper maxillary support such that said prop stem and said upper maxillary support are in threaded engagement, whereby relative rotation of said upper maxillary support and said prop stem adjusts the axial distance therebetween.

9. The dental device of 7, wherein said movable adjusting means includes a threaded stud extending from said top section of said prop stem and a mating internally threaded sleeve extending from said upper maxillary support such that said prop stem and said upper maxillary support are in threaded engagement, and further comprising means for rotatively coupling said upper maxillary support to said threaded sleeve, whereby relative rotation of said threaded sleeve and said threaded stud adjusts the axial distance between said upper maxillary support and said prop stem without relative rotation therebetween.

10. The dental device of claim 7, wherein said upper maxillary support comprises a U-shaped member for supporting the patient's maxillary arch.

11. The dental device of claim 1, wherein said prop stem comprises a first sidewall defining a first conduit therethrough and a first aperture in said first sidewall in communication with said first conduit, and wherein said buccal member comprises a second sidewall defining a second conduit therethrough and a second aperture in said second sidewall in communication with said second conduit, said first and second conduits being in fluid communication such that fluids may be channeled through a fluid circuit comprising said first and second conduits and said first and second apertures.

12. The dental device of claim 1, wherein said prop stem comprises a first sidewall defining a first conduit therethrough and a first aperture in said first sidewall in communication with said first conduit, and wherein said lingual member comprises a second sidewall defining a second conduit therethrough and a second aperture in said second sidewall in communication with said second conduit, said first and second conduits being in fluid communication such that fluids may be channeled through a fluid circuit comprising said first and second conduits and said first and second apertures.

13. The dental device of claim 12, wherein said lingual member comprises a third sidewall defining a third conduit therethrough and a third aperture in said third sidewall in communication with said third conduit, said first conduit being in fluid communication with said third conduit such that fluids may be channeled through another fluid circuit comprising said first and third conduits and said first and third apertures.

* * * * *